(12) United States Patent
Jetti et al.

(10) Patent No.: US 9,815,789 B2
(45) Date of Patent: Nov. 14, 2017

(54) POLYMORPHS OF CABOZANTINIB (S)-MALATE AND CABOZANTINIB FREE BASE

(71) Applicant: Mylan Labs Limited, Hyderabad (IN)

(72) Inventors: Ramakoteswara Rao Jetti, Hyderabad (IN); Anjaneyaraju Indukuri, Hyderabad (IN); Dnyandeo Punde, Hyderabad (IN); Chandersingh Bohra, Hyderabad (IN); Mahesh Kumar Gadakar, Hyderabad (IN); Vinayak Gore, Hyderabad (IN)

(73) Assignee: Mylan Laboratories, Ltd. (IN)

( * ) Notice: Subject to any disclaimer, the term of this patent is extended or adjusted under 35 U.S.C. 154(b) by 0 days.

(21) Appl. No.: 15/313,191

(22) PCT Filed: May 22, 2015

(86) PCT No.: PCT/IB2015/053765
§ 371 (c)(1),
(2) Date: Nov. 22, 2016

(87) PCT Pub. No.: WO2015/177758
PCT Pub. Date: Nov. 26, 2015

(65) Prior Publication Data
US 2017/0096395 A1    Apr. 6, 2017

(30) Foreign Application Priority Data

May 23, 2014 (IN) .......................... 2561/CHE/2014

(51) Int. Cl.
*C07D 215/233* (2006.01)

(52) U.S. Cl.
CPC ...... *C07D 215/233* (2013.01); *C07B 2200/13* (2013.01)

(58) Field of Classification Search
CPC ................ C07D 215/233; C07B 2200/13
See application file for complete search history.

(56) References Cited

U.S. PATENT DOCUMENTS 7,579,473 B2    8/2009    Bannen et al.
8,877,776 B2    11/2014    Brown et al.

FOREIGN PATENT DOCUMENTS

WO    2010083414    *    7/2010

* cited by examiner

*Primary Examiner* — D M Seaman

(57) ABSTRACT

The present disclosure provides novel crystalline forms of cabozantinib (S)-malate, designated as form-$M_1$, $M_2$, $M_3$ and $M_4$ and novel crystalline forms of cabozantinib free base, form-$M_1$, $M_2$ and $M_3$ and methods of their production. The present disclosure also provides processes for the preparation of crystalline cabozantinib (S)-malate form N-1.

17 Claims, 17 Drawing Sheets

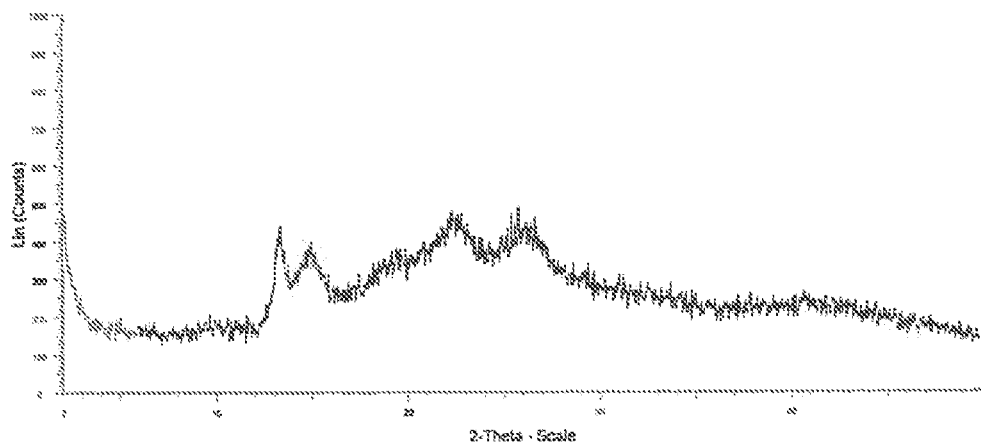
FIGURE 1-Powder x-ray diffraction pattern of crystalline cabozantinib (S)-malate form-M₂

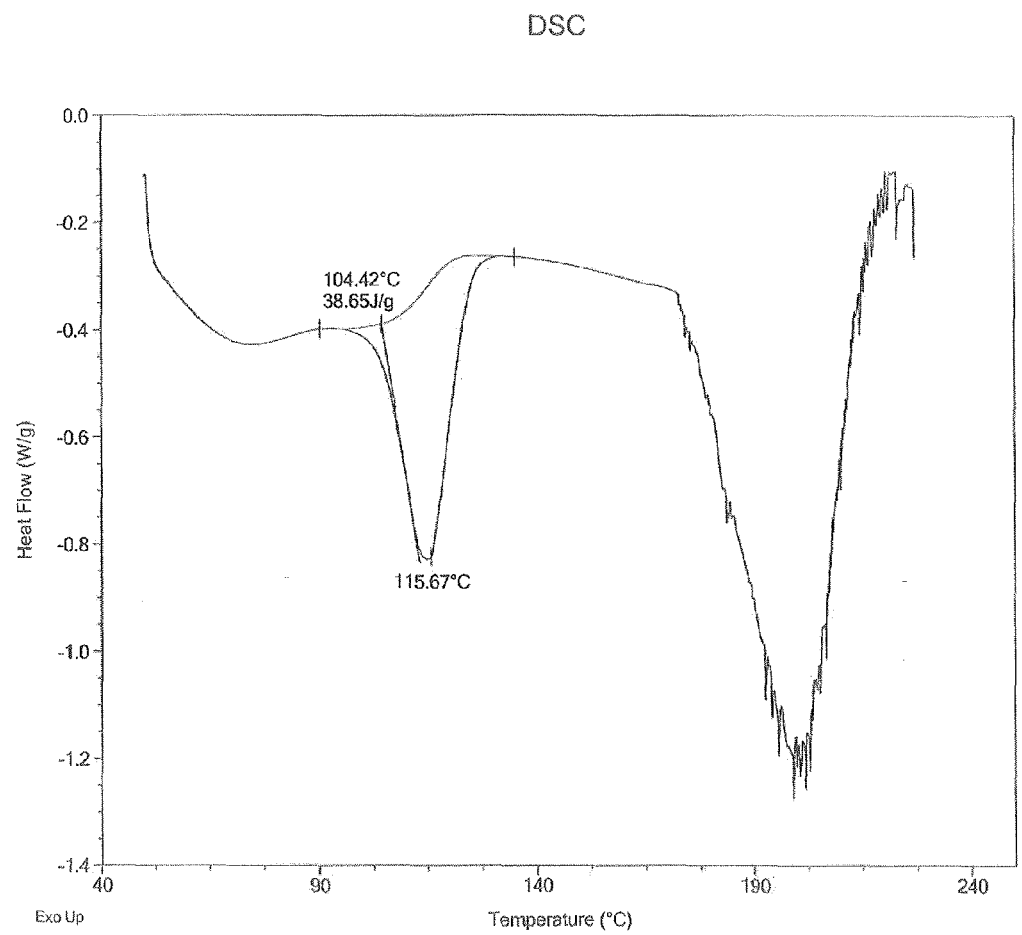
FIGURE 2 - DSC thermogram of crystalline cabozantinib (S)-malate form-M$_1$

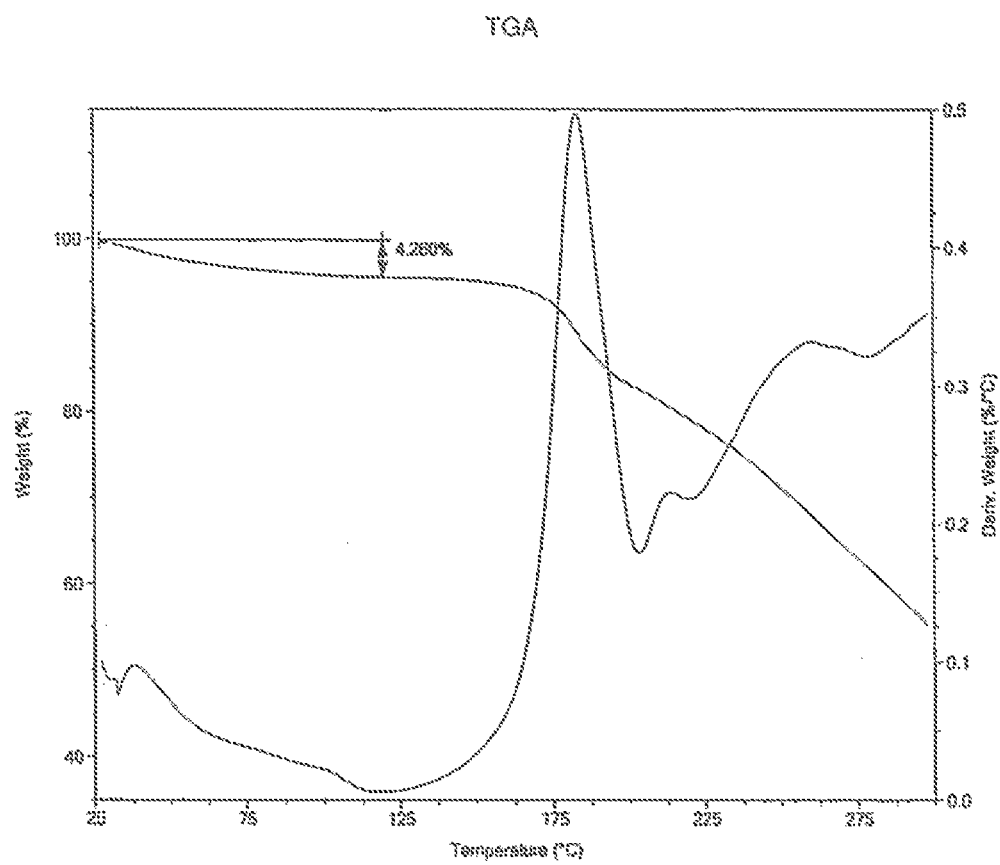
FIGURE 3 – TGA trace of crystalline cabozantinib (S)-malate form-M₁

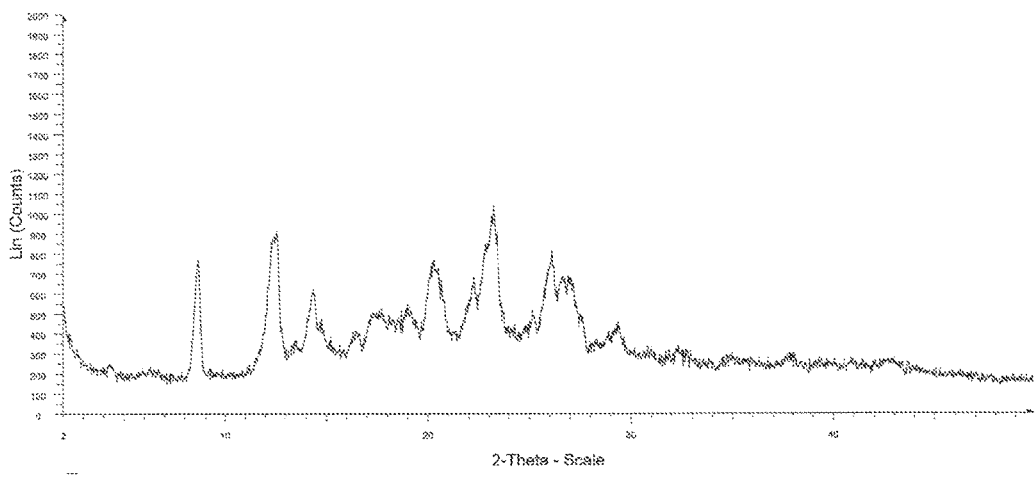
FIGURE 4 - Powder x-ray diffraction pattern of crystalline cabozantinib (S)-malate form-M₂

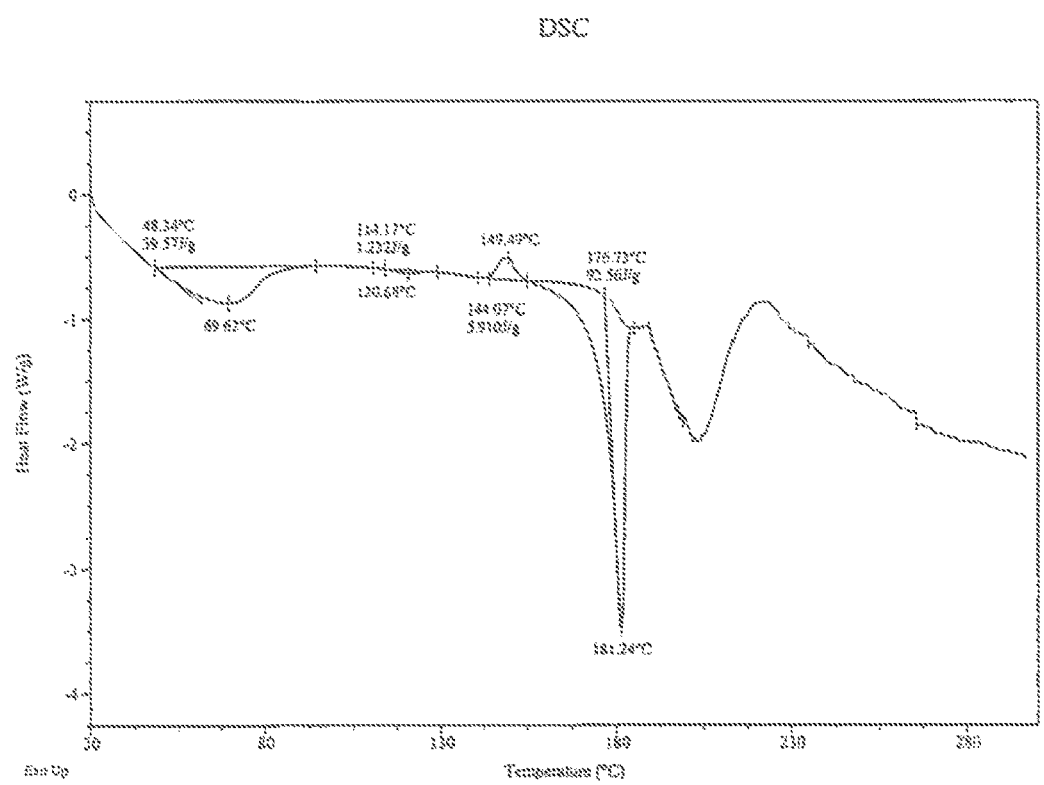
FIGURE 5 - DSC thermogram of crystalline cabozantinib (S)-malate form-$M_2$

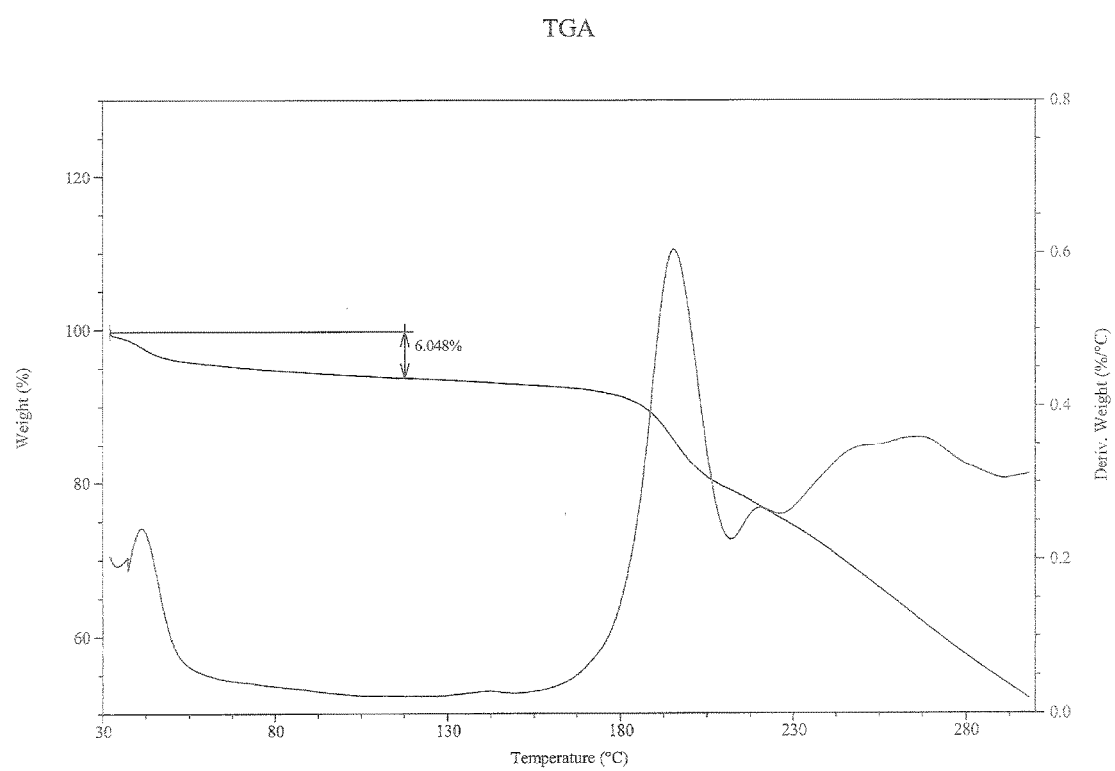
FIGURE 6 - TGA trace of crystalline cabozantinib (S)-malate form-M₂

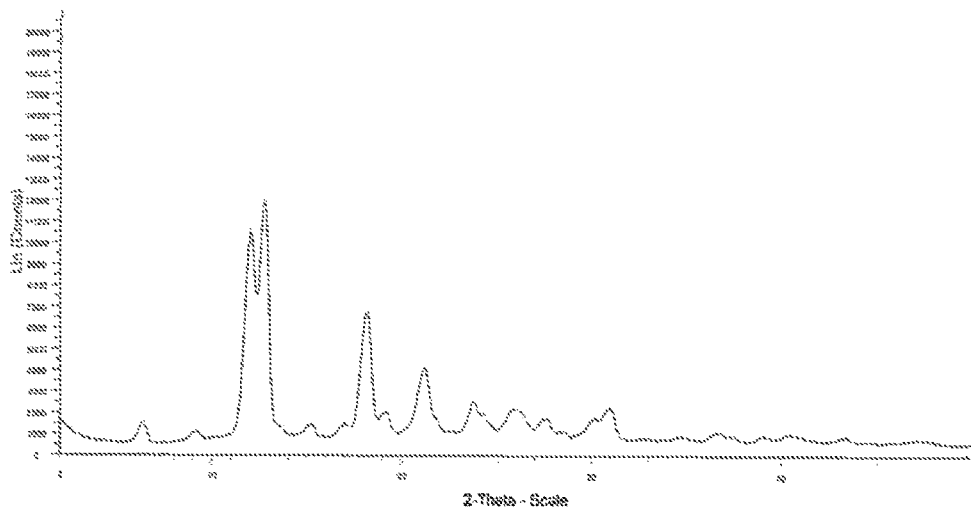
FIGURE 7 - Powder x-ray diffraction pattern of crystalline cabozantinib (S)-malate form-$M_3$

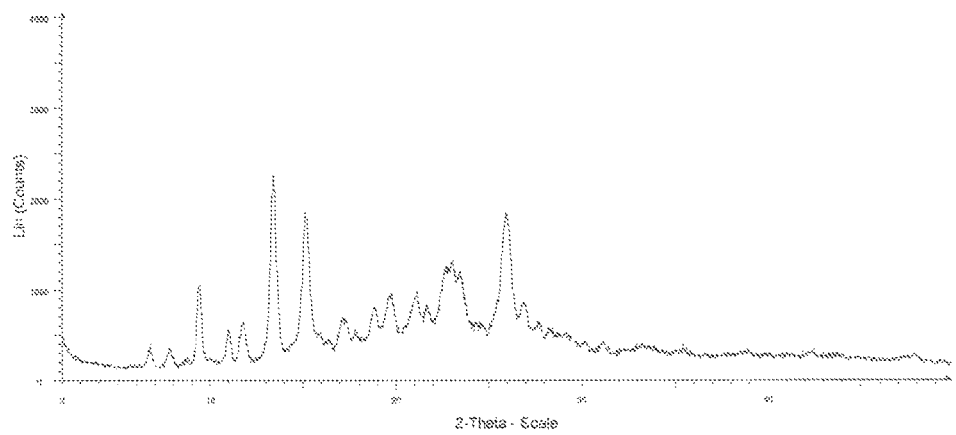
FIGURE 8 - Powder x-ray diffraction pattern of crystalline cabozantinib (S)-malate form-$M_4$

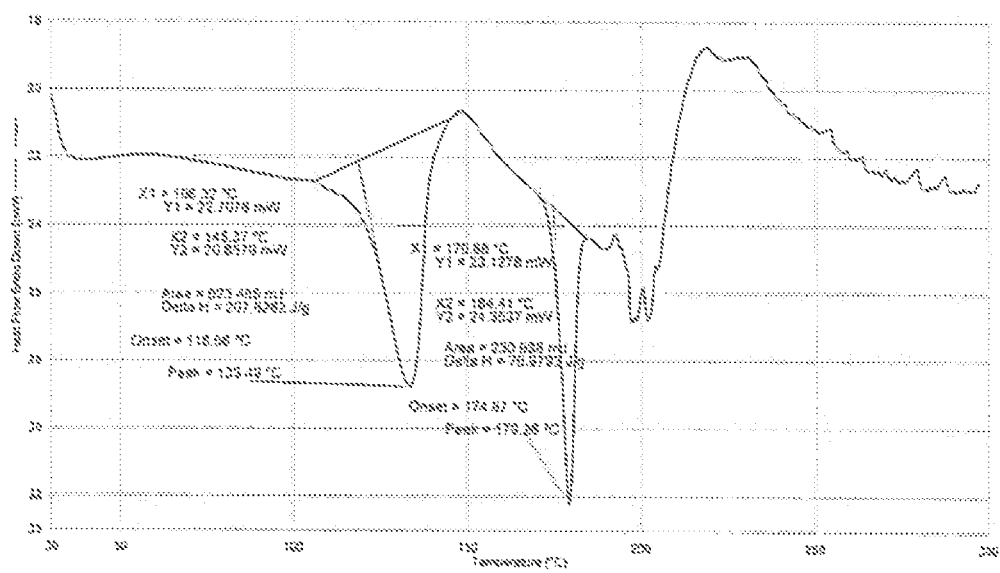
FIGURE 9 - DSC thermogram of crystalline cabozantinib (S)-malate form-M₄

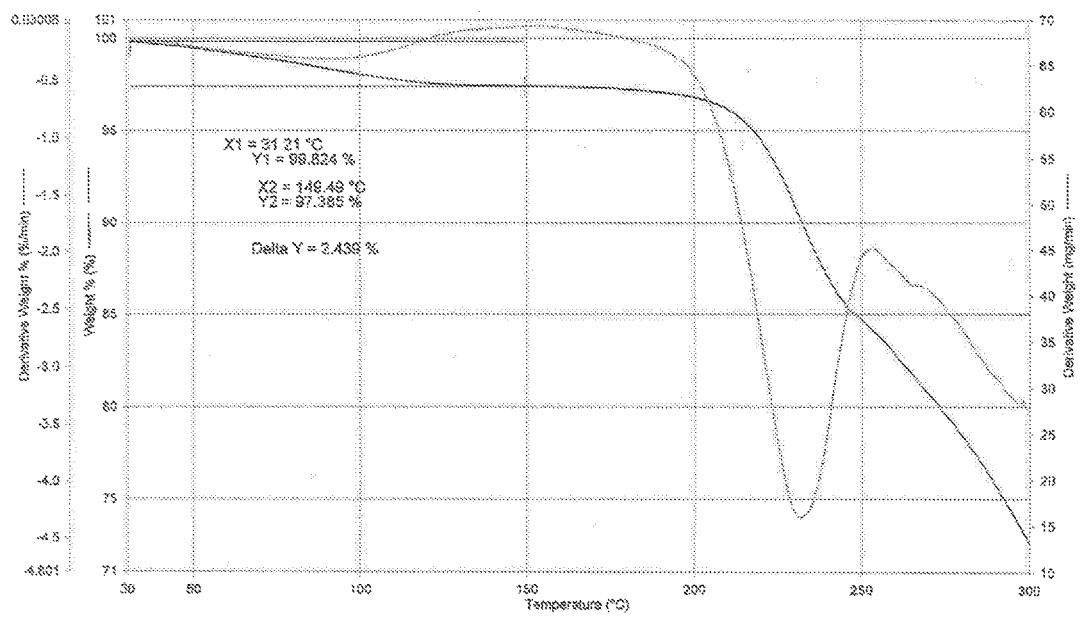
FIGURE 10 - TGA trace of crystalline cabozantinib (S)-malate form-M₄

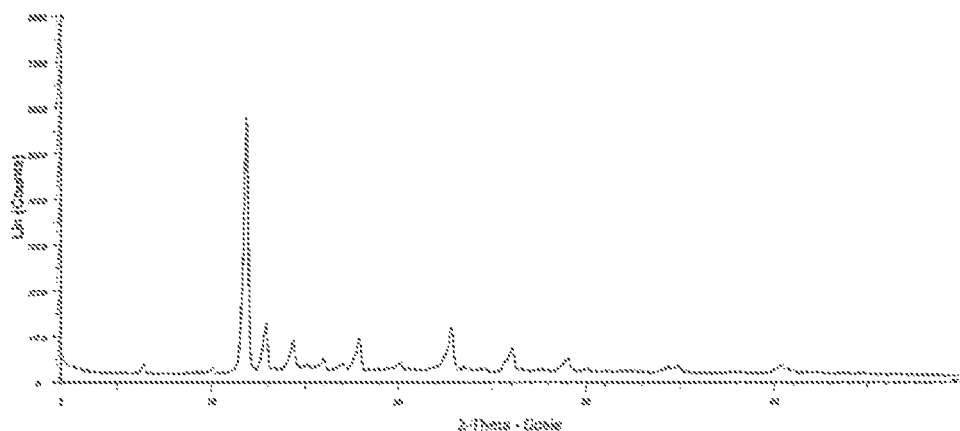
FIGURE 11 - Powder x-ray diffraction pattern of crystalline cabozantinib free base form-M₃

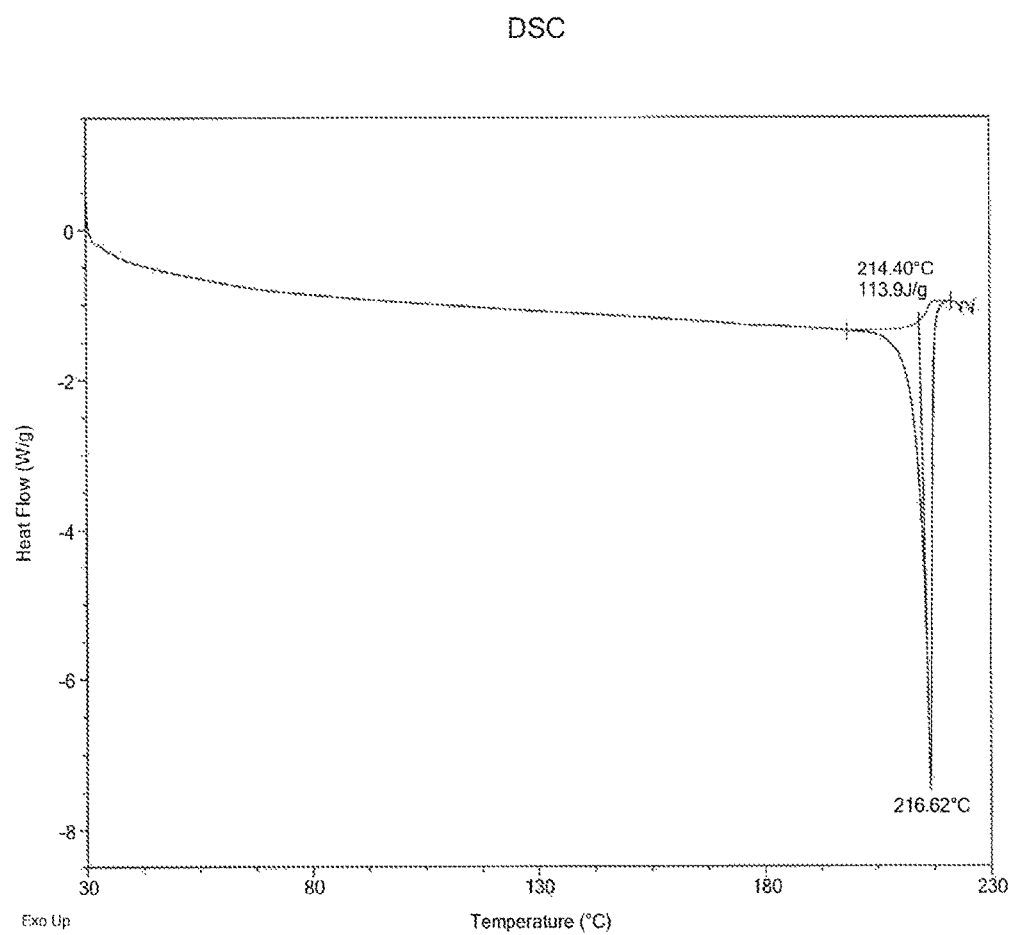
FIGURE 12 - DSC thermogram of crystalline cabozantinib free base form-$M_1$

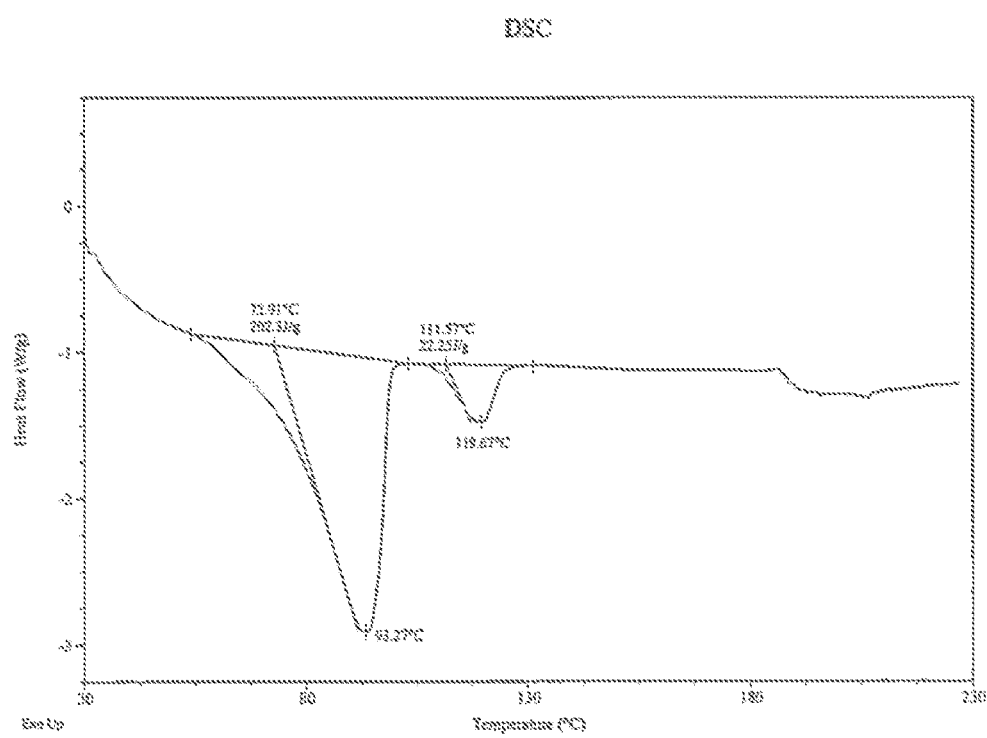
FIGURE 13 - TGA trace of crystalline cabozantinib free base form-M₁

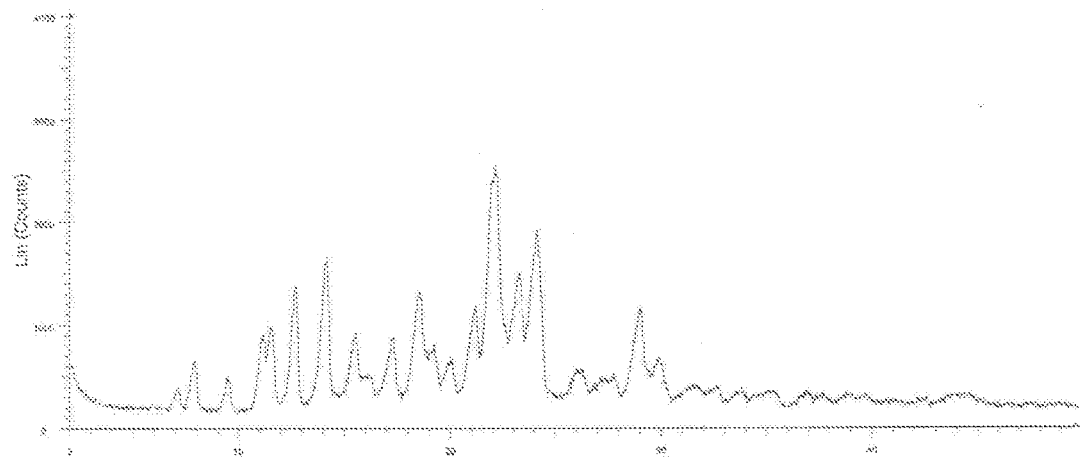
FIGURE 14 - Powder x-ray diffraction pattern of crystalline cabozantinib free base form-M₂

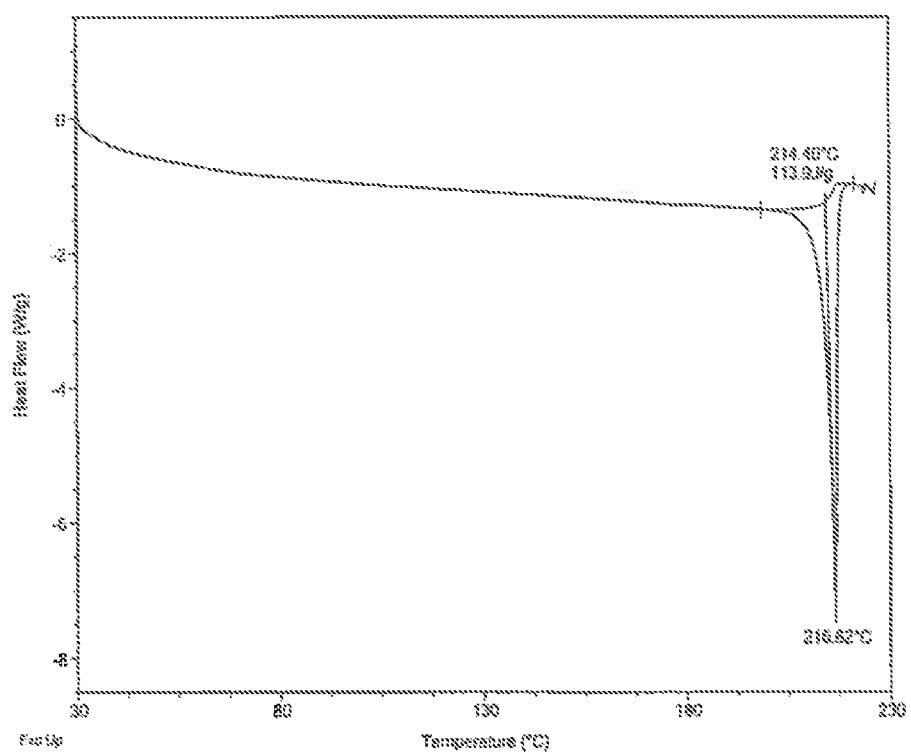
FIGURE 15 - DSC thermogram of crystalline cabozantinib free base form-$M_2$

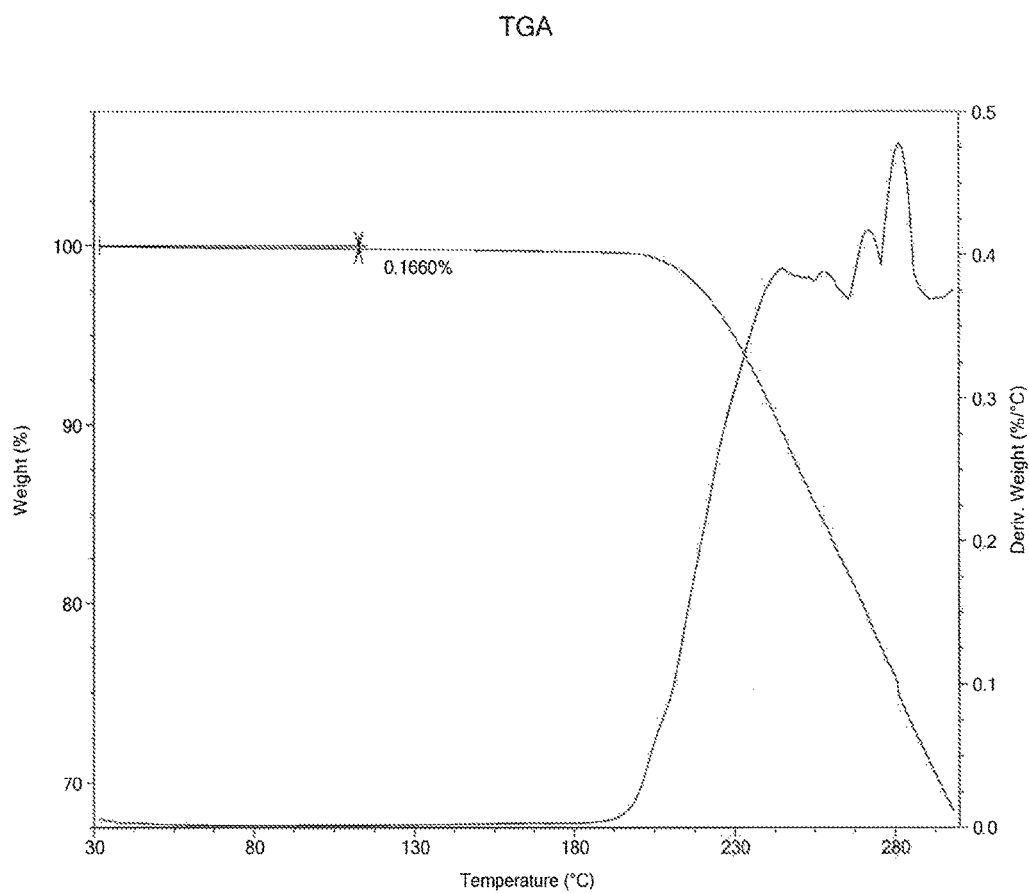
FIGURE 16 - TGA trace of crystalline cabozantinib free base form-M₂

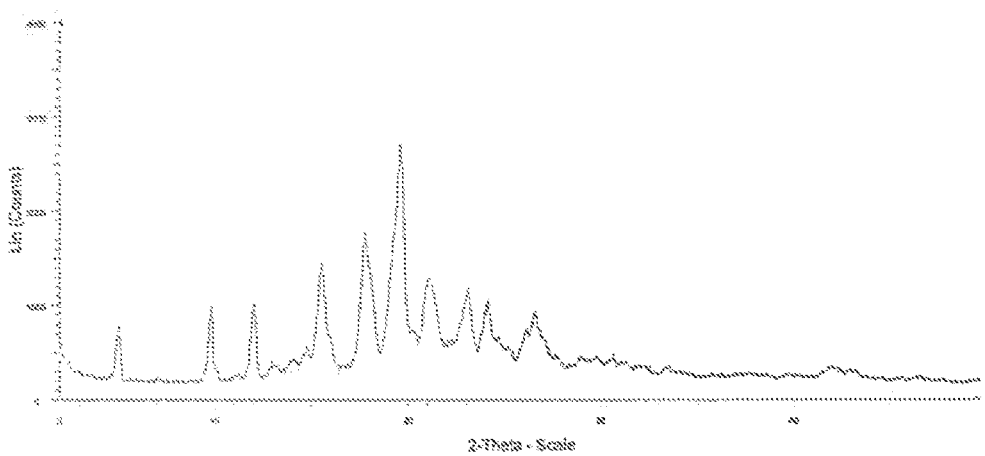
FIGURE 17 – Powder x-ray diffraction pattern of crystalline cabozantinib free base form-$M_3$

POLYMORPHS OF CABOZANTINIB (S)-MALATE AND CABOZANTINIB FREE BASE

CROSS-REFERENCE TO RELATED APPLICATIONS

This application, in its entirety, claims the benefit of earlier Indian provisional patent application No 2561/CHE/2014 filed on May 23, 2014.

BACKGROUND OF THE INVENTION

Field of the Invention

The present invention relates generally to novel crystalline forms of cabozantinib (S)-malate, designated as form-$M_1$, $M_2$, $M_3$, and $M_4$ and novel crystalline forms of cabozantinib free base, form-$M_1$, $M_2$ and $M_3$. The present invention also relates to process for the preparation of crystalline forms of cabozantinib (S)-malate, designated as form-$M_1$, $M_2$, $M_3$, and $M_4$ and novel crystalline forms of cabozantinib free base, form-$M_1$, $M_2$ and $M_3$ as well as crystalline cabozantinib (S)-malate form N-1.

Background of the Invention

Cabozantinib (S)-malate, chemically known as N-(4-(6,7-dimethoxyquinolin-4-yloxy)phenyl)-N'-(4-fluorophenyl) cyclopropane-1,1-dicarboxamide (S)-malate is structurally represented as Formula-I below. Cabozantinib is marketed under the trade name COMETRIQ® by Exelixis, Inc. COMETRIQ® is indicated for the treatment of patients with progressive, metastatic medullary thyroid cancer.

Formula-I

The chemical structure of cabozantinib is disclosed in U.S. Pat. No. 7,579,473, which is hereby incorporated by reference. U.S. Pat. No. 8,877,776, which is also hereby incorporated by reference, discloses amorphous forms of cabozantinib L- and D-malate as well as the N-1 and N-2 polymorphs of crystalline cabozantinib L- and D-malate.

The present invention provides novel crystalline forms of cabozantinib (S)-malate and novel crystalline forms of cabozantinib free base.

SUMMARY OF THE INVENTION

One aspect of the present invention provides novel crystalline forms-$M_1$, $M_2$, $M_3$ and $M_4$ of cabozantinib (S)-malate.

One embodiment of the present invention provides a process for the preparation of crystalline form-$M_1$ of cabozantinib (S)-malate which includes the steps of:
a) dissolving cabozantinib (S)-malate in a solvent or mixture of solvents,
b) adding the above solution of step (a) to non-polar solvent, and
c) isolating the crystalline form-$M_1$ of cabozantinib (S)-malate.

Another embodiment of the present invention provides a process for the preparation of crystalline form-$M_1$ of cabozantinib (S)-malate which includes the steps of:
a) dissolving cabozantinib base and (S)-malic acid in a solvent or mixture of solvents,
b) adding the above solution of step (a) to non-polar solvent, and
c) isolating the crystalline form-$M_1$ of cabozantinib (S)-malate.

Another embodiment of the present invention a process for the preparation of crystalline form-$M_2$ of cabozantinib (S)-malate which includes the steps of:
a) dissolving cabozantinib (S)-malate in a polar solvent,
b) adding an ethereal solvent, and
c) isolating the crystalline form-$M_2$ of cabozantinib (S)-malate.

Another embodiment of the present invention provides a process for the preparation of crystalline form-$M_3$ of cabozantinib (S)-malate which includes the steps of:
a) dissolving cabozantinib (S)-malate in a polar solvent,
b) adding water, and
c) isolating the crystalline form-$M_3$ of cabozantinib (S)-malate.

Another embodiment of the present invention provides a process for the preparation of crystalline form-$M_4$ of cabozantinib (S)-malate which includes the steps of:
a) dissolving cabozantinib base and (S)-malic acid in a solvent to create a solution,
b) adding the solution to a non-polar solvent, and
c) isolating the crystalline form-$M_4$ of cabozantinib (S)-malate.

Another embodiment of the present invention provides a process for the preparation of crystalline form-$M_4$ of cabozantinib (S)-malate which includes the steps of:
a) dissolving cabozantinib (S)-malate in an amide solvent,
b) adding a solvent to the reaction mixture, and
c) isolating the crystalline form-$M_4$ of cabozantinib (S)-malate.

Another aspect of the present invention provides novel crystalline forms-$M_1$, $M_2$ and $M_3$ of cabozantinib free base.

One embodiment of the present invention provides a process for the preparation of crystalline form-$M_1$ of cabozantinib free base which includes the steps of:
a) dissolving cabozantinib (S)-malate in a solvent to create a solution,
b) adding water to the solution,
c) adding ketone solvent, and
d) isolating the crystalline form-$M_1$ of cabozantinib free base.

Another embodiment of the present invention provides a process for the preparation of crystalline form-$M_1$ of cabozantinib free base which includes the steps of:
a) dissolving cabozantinib (S)-malate in a solvent to create a solution,
b) adding water to the solution, and
c) isolating the crystalline form-$M_1$ of cabozantinib free base.

Another embodiment of the present invention provides a process for the preparation of crystalline form-$M_2$ of cabozantinib free base which includes the steps of:
a) dissolving cabozantinib in a solvent, b) partially removing the solvent, and
c) isolating the crystalline form-$M_2$ of cabozantinib free base Another embodiment of the present invention provides a process for the preparation of crystalline form-$M_3$ of cabozantinib free base which includes the steps of:
a) providing cabozantinib base in an ester solvent,
b) removing the ester solvent,
c) adding an ethereal solvent, and
d) isolating the crystalline form-$M_3$ of cabozantinib free base.

Yet another aspect of the present invention provides a process for the preparation of crystalline cabozantinib (S)-malate form N-1 which includes the steps of:
a) providing cabozantinib base and (S)-malic acid in a first polar solvent,
b) adding second solvent,
c) seeding with form N-1 of cabozantinib (S)-malate, and
d) isolating the cabozantinib (S)-malate form N-1.

BRIEF DESCRIPTION OF THE DRAWINGS

Further objects of the present invention together with additional features contributing thereto and advantages accruing there from will be apparent from the following description of preferred embodiments of the invention which are shown in the accompanying drawing figures wherein:

FIG. 1 is a powder X-ray diffraction pattern of crystalline cabozantinib (S)-malate form-$M_1$;

FIG. 2 is a DSC thermogram of crystalline cabozantinib (S)-malate form-$M_1$;

FIG. 3 is a TGA trace of crystalline cabozantinib (S)-malate form-$M_1$;

FIG. 4 is a powder X-ray diffraction pattern of crystalline cabozantinib (S)-malate form-$M_2$;

FIG. 5 is a DSC thermogram of crystalline cabozantinib (S)-malate form-$M_2$;

FIG. 6 is a TGA trace of crystalline cabozantinib (S)-malate form-$M_2$;

FIG. 7 is a powder X-ray diffraction pattern of crystalline cabozantinib (S)-malate form-$M_3$;

FIG. 8 is a powder X-ray diffraction pattern of crystalline cabozantinib (S)-malate form-$M_4$;

FIG. 9 is a DSC thermogram of crystalline cabozantinib (S)-malate form-$M_4$;

FIG. 10 is a TGA trace of crystalline cabozantinib (S)-malate form-$M_4$;

FIG. 11 is a powder X-ray diffraction pattern of crystalline cabozantinib free base form-$M_1$;

FIG. 12 is a DSC thermogram of crystalline cabozantinib free base form-$M_1$;

FIG. 13 is a TGA trace of crystalline cabozantinib free base form-$M_1$;

FIG. 14 is a powder X-ray diffraction pattern of crystalline cabozantinib free base form-$M_2$;

FIG. 15 is a DSC thermogram of crystalline cabozantinib free base form-$M_2$;

FIG. 16 is a TGA trace of crystalline cabozantinib free base form-$M_2$; and

FIG. 17 is a powder X-ray diffraction pattern of crystalline cabozantinib free base form-$M_3$.

DETAILED DESCRIPTION OF THE INVENTION

It is to be understood that the description of the present invention has been simplified to illustrate elements that are relevant for a clear understanding of the invention, while eliminating, for purposes of clarity, other elements that may be well known.

The present disclosure provides novel crystalline forms-$M_1$, $M_2$, $M_3$ and $M_4$ of cabozantinib (S)-malate and crystalline forms-$M_1$, $M_2$ and $M_3$ of cabozantinib free base. The present disclosure also provides processed for the preparation of crystalline forms-$M_1$, $M_2$, $M_3$ and $M_4$ of cabozantinib (S)-malate and crystalline forms-$M_1$, $M_2$ and $M_3$ of cabozantinib free base as well as crystalline cabozantinib (S)-malate form N-1.

One aspect of the present invention provides crystalline form-$M_1$ of cabozantinib (S)-malate.

One embodiment of the present invention provides a process for the preparation of crystalline form-$M_1$ of cabozantinib (S)-malate which includes the following steps:
a) dissolving cabozantinib (S)-malate in a solvent to create a solution,
b) adding the above solution of step (a) to a non-polar solvent, and
c) isolating the crystalline form-$M_1$ of cabozantinib (S)-malate.

According to the present invention, cabozantinib (S)-malate may be dissolved in a solvent to create a solution. Within the context of the present invention, the solvent used for dissolving cabozantinib (S)-malate may be, for example, ethereal, alcoholic, water, or mixtures thereof. Examples of suitable ethereal solvents include dimethyl ether, diethyl ether, ethyl methyl ether, methyl-tert-butyl ether, tetrahydrofuran, and 1,4-dioxane. Suitable alcohols include, for example, methanol, ethanol, propanol, and butanol. In certain embodiments, a mixture of tetrahydrofuran and water was found to be a particularly useful solvent for dissolving cabozantinib (S)-malate.

Next, the solution of cabozantinib (S)-malate may be added to a non-polar solvent. The non-polar solvent may be, for example, a $C_1$-$C_{10}$ alkane or a mixture of $C_1$-$C_{10}$ alkanes. In certain embodiments, n-heptane was found to be a particularly useful non-polar solvent. The obtained solid may then be isolated to get a crystalline form-$M_1$ of cabozantinib (S)-malate.

In particularly useful embodiments of the present invention, cabozantinib (S)-malate may be dissolved in tetrahydrofuran and water at a temperature of about 55° C. to about 70° C. The reaction temperature may then be cooled to room temperature. The resulting clear solution may then be added to a non-polar solvent such as n-heptane. The obtained solid may be filtered and dried to get the crystalline form-$M_1$ of cabozantinib (S)-malate.

Another embodiment of the present invention provides a process for the preparation of crystalline form-$M_1$ of cabozantinib (S)-malate which includes the following steps:
a) dissolving cabozantinib base and (S)-malic acid in a solvent to create a solution,
b) adding the above solution of step (a) to non-polar solvent, and
c) isolating the crystalline form-$M_1$ of cabozantinib (S)-malate.

According to the present invention, cabozantinib base and (S)-malic acid may be dissolved in a solvent. Within the context of the present invention, the solvent may be, for example, an ethereal solvent, an alcoholic solvent, water, or a mixture thereof. Examples of suitable ethereal solvents include dimethyl ether, diethyl ether, ethyl methyl ether, methyl-tert-butyl ether, tetrahydrofuran, and 1,4-dioxane. Examples of suitable alcohols include methanol, ethanol, propanol, and butanol. In some embodiments of the present invention, a mixture of tetrahydrofuran and water was found to be particularly useful. In some embodiments, tetrahydrofuran and water in a ratio of 12:1 was found to be particularly useful.

Next, the solution of cabozantinib (S)-malate may be added to a non-polar solvent. The non-polar solvent may be, for example, a $C_1$-$C_{10}$ alkane or a mixture of $C_1$-$C_{10}$ alkanes. In certain embodiments, n-heptane was found to be a particularly useful non-polar solvent. The obtained solid may then be isolated to get a crystalline form-$M_1$ of cabozantinib (S)-malate.

In particularly useful embodiments of the present invention, cabozantinib base and (S)-malic acid may be dissolved in a mixture of solvents such as tetrahydrofuran and water at a temperature between about 55° C. to about 70° C. The temperature of the solution may then be cooled to room temperature. The resulting clear solution may then be added to non-polar solvent, for example, n-heptane, at about 20° C. to about 35° C. The obtained solid may then be filtered and dried under vacuum to get the crystalline form-$M_1$ of cabozantinib (S)-malate.

The crystalline polymorph forms of compounds disclosed in the present invention may be characterized by X-ray powder diffraction ("XRPD") pattern. Thus, the XRPD patterns of the polymorphs of the present disclosure were measured.

The XRPD patterns were measured on BRUKER D-8 Discover powder diffractometer equipped with goniometer of θ/2θ configuration and Lynx Eye detector. The Cu-anode X-ray tube was operated at 40 kV and 30 mA. The experiments were conducted over the 2θ range of 2.0°-50.0°, 0.030° step size and 0.4 seconds step time.

According to the present invention, crystalline form-$M_1$ of cabozantinib (S)-malate may be characterized by an XRPD pattern having characteristic peak at about 13.2(±) 0.2° 2-theta.

Within the context of the present invention, the crystalline form-$M_1$ of cabozantinib (S)-malate may be further characterized by the XRPD pattern in FIG. 1.

The crystalline polymorph forms of compounds disclosed in the present invention may also be characterized by differential scanning calorimetry (DSC). Thus, DSC thermograms of the polymorphs of the disclosure were measured.

The DSC measurements were carried out on TA Q1000 of TA Instruments. The experiments were performed at a heating rate of 20.0° C./min over a temperature range of 30° C.-330° C. purging with nitrogen at a flow rate of 50 ml/min. Standard aluminum crucibles covered by lids with pin holes were used.

According to the present invention, the crystalline form-$M_1$ of cabozantinib (S)-malate may be characterized by the DSC thermogram in FIG. 2.

The crystalline polymorph forms of compounds disclosed in the present invention may also be characterized by thermogravimetric analysis (TGA). Thus, the TGA/DTA traces of the polymorphs of the disclosure were measured.

TGA/DTA was recorded using the instrument TA Q5000 IR of TA Instruments. The experiments were performed at a heating rate of 10.0° C./min over a temperature range of 30° C.-350° C. purging with nitrogen at a flow rate of 25 ml/min.

According to the present invention, the crystalline form-$M_1$ of cabozantinib (S)-malate may be characterized by the TGA trace in FIG. 3.

Another aspect of the present invention provides crystalline form-$M_2$ of cabozantinib (S)-malate.

One embodiment of the present invention provides a process for the preparation of crystalline form-$M_2$ of cabozantinib (S)-malate which includes the following steps:
  a) dissolving cabozantinib (S)-malate in a polar solvent to create a solution,
  b) adding an ethereal solvent to the solution, and
  c) isolating the crystalline form-$M_2$ of cabozantinib (S)-malate.

According to the present invention, cabozantinib (S)-malate may be dissolved in a polar solvent. Within the context of the present invention, the polar solvent may be, for example, formic acid, acetic acid, or propionic acid. In some embodiments of the present invention, propionic acid is a particularly useful solvent.

Next, an ethereal solvent may be added to the reaction mass. Within the context of the present invention, the ethereal solvent may be, for example, dimethyl ether, diethyl ether, ethyl methyl ether, methyl-t-butyl ether, tetrahydrofuran, or 1,4-dioxane. In some embodiments, methyl-t-butyl ether was found to be a particularly useful solvent. Crystalline form-$M_2$ of cabozantinib (S)-malate may then be isolated.

In particularly useful embodiments of the present invention, cabozantinib (S)-malate may be dissolved in a polar solvent such as propionic acid at temperature about 45° C. to about 55° C. and then cooled to about 20° C. to about 35° C. An ethereal solvent such as methyl-t-butyl ether may then be added to the reaction mixture. The obtained solid may then be filtered and dried to get the crystalline form-$M_2$ of cabozantinib (S)-malate.

According to the present invention, crystalline form-$M_2$ of cabozantinib (S)-malate may be characterized by the XRPD pattern having characteristic peaks at 8.5, 12.5, 20.2, 23.1, and 26.1 (±) 0.2° 2-theta.

Within the context of the present invention, crystalline form-$M_2$ of cabozantinib (S)-malate may be further characterized by XRPD pattern having characteristic peaks at 8.5, 12.5, 14.3, 20.2, 22.2, 23.1, 26.1, 26.6, and 26.9(±)0.2° 2-theta.

Within the context of the present invention, the crystalline form-$M_2$ of cabozantinib (S)-malate may be further characterized by the XRPD pattern in FIG. 4.

The crystalline form-$M_2$ of cabozantinib (S)-malate may also be characterized by the DSC thermogram in FIG. 5.

The crystalline form-$M_2$ of cabozantinib (S)-malate may additionally be characterized by the TGA trace in FIG. 6.

Another aspect of the present invention provides crystalline form-$M_3$ of cabozantinib (S)-malate.

One embodiment of the present invention provides a process for the preparation of crystalline form-$M_3$ of cabozantinib (S)-malate which includes the following steps:
  a) dissolving cabozantinib (S)-malate in a polar solvent to create a solution,
  b) adding water to the solution, and
  c) isolating the crystalline form-$M_3$ of cabozantinib (S)-malate.

According to the present invention, cabozantinib (S)-malate may be dissolved in a polar solvent. Within the context of the present invention, the polar solvent may be, for example, formic acid, acetic acid, or propionic acid. In certain embodiments, acetic acid was found to be a particularly useful polar solvent. Next, water is added to the reaction mass and crystalline form-$M_3$ of cabozantinib (S)-malate may then be isolated.

In particularly useful embodiments of the present invention, cabozantinib (S)-malate may be dissolved in a polar solvent, such as acetic acid, at a temperature between about 55° C. and about 65° C. The resulting clear solution may be cooled to about −5° C. to about 10° C., and water may be added to the reaction mass. The obtained solid may then be filtered and washed with water to get the crystalline form-$M_3$ of cabozantinib (S)-malate.

According to the present invention, crystalline form-$M_3$ of cabozantinib (S)-malate may be characterized by the XRPD pattern having characteristic peaks, 11.9, 12.6, and 18.1(±)0.2° 2-theta.

Within the context of the present invention, crystalline form-$M_3$ of cabozantinib (S)-malate may be further characterized by the XRPD pattern having characteristic peaks at 6.3, 9.1, 11.9, 12.6, 13.6, 15.1, 16.9, 18.1, 19.1, 21.2, 23.7, 25.8, 27.5, 30.1, and 31.0(±)0.2° 2-theta.

The crystalline form-$M_3$ of cabozantinib (S)-malate may also be further characterized by the powder X-ray diffractogram in FIG. 7.

Another aspect of the present invention provides the crystalline form-$M_4$ of cabozantinib (S)-malate.

One embodiment of the present invention provides a process for the preparation of crystalline form-$M_4$ of cabozantinib (S)-malate which includes the following steps:
 a) dissolving cabozantinib base and (S)-malic acid in a solvent to create a solution,
 b) adding the above solution of step (a) to a non-polar solvent,
 c) isolating the crystalline form-$M_4$ of cabozantinib (S)-malate.

According to the present invention, cabozantinib base and (S)-malic acid may be dissolved in a solvent. Within the context of the present invention, the solvent may be, for example, an ethereal solvent, an alcoholic solvent, water, or a mixture thereof. Examples of suitable ethereal solvents include dimethyl ether, diethyl ether, ethyl methyl ether, methyl-tert-butyl ether, tetrahydrofuran, and 1,4-dioxane. Suitable alcohols include, for example, methanol, ethanol, propanol, and butanol. In some embodiments of the present invention, a mixture of tetrahydrofuran and water was found to be particularly useful. In some embodiments, a ratio of 15:1 tetrahydrofuran to water was found to be particularly useful.

Next, the solution of cabozantinib (S)-malate may be added to a non-polar solvent. The non-polar solvent may be, for example, a $C_1$-$C_{10}$ alkane or a mixture of $C_1$-$C_{10}$ alkanes. In certain embodiments, n-heptane was found to be a particularly useful non-polar solvent. The obtained solid may then be isolated to get a crystalline form-$M_4$ of cabozantinib (S)-malate.

In particularly useful embodiments of the present invention, cabozantinib base and (S)-malic acid may be dissolved in a mixture of solvents, such as tetrahydrofuran and water, at a temperature between about 55° C. and about 70° C. The reaction temperature may then be cooled to room temperature. The resulted clear solution may then be added to a non-polar solvent, for example, n-heptane, at about 45° C. to about 60° C. The resulted reaction mass may be cooled to about 20° C. to about 35° C. The obtained solid is filtered and dried under vacuum to get the crystalline form-$M_4$ of cabozantinib (S)-malate.

Another embodiment of the present invention provides a process for the preparation of crystalline form-$M_4$ of cabozantinib (S)-malate which includes the following steps:
 a) dissolving cabozantinib (S)-malate in an amide solvent to create a solution,
 b) adding a solvent to the solution, and
 c) isolating the crystalline form-$M_4$ of cabozantinib (S)-malate.

According to the present invention, cabozantinib (S)-malate may be dissolved in an amide solvent to create a solution. Within the context of the present invention, the amide solvent may be, for example, N,N-dimethylacetamide, N,N-dimethylformamide, or N-methylpyrrolidone. In some embodiments of the present invention, N,N-dimethylacetamide was found to be a particularly useful solvent.

Next, a solvent may be added to the solution. Within the context of the present invention, the solvent may be, for example, an ethereal solvent, an alcoholic solvent, water, or mixtures thereof. Examples of suitable ethereal solvents include dimethyl ether, diethyl ether, ethyl methyl ether, methyl-t-butyl ether, tetrahydrofuran, and 1,4-dioxane. Examples of suitable alcohol solvents include methanol, ethanol, propanol, and butanol. In some embodiments, a mixture of methyl-t-butyl ether and ethanol was found to be particularly useful. Next, the solid may be isolated to get a crystalline form-$M_4$ of cabozantinib (S)-malate.

In particularly useful embodiments of the present invention, cabozantinib (S)-malate may be dissolved in an amide solvent such as N,N-dimethylacetamide at a temperature between about 45° C. and about 55° C. to create a clear solution. Methyl-t-butyl ether and ethanol may then be added to the clear solution at room temperature. The obtained solid may then be filtered and dried to get the crystalline form-$M_4$ of cabozantinib (S)-malate.

According to the present invention, crystalline form-$M_4$ of cabozantinib (S)-malate may be characterized by the XRPD pattern having characteristic peaks at about 13.3, 15.0, 22.8, and 25.8 (±) 0.2° 2-theta.

The crystalline form-$M_4$ of cabozantinib (S)-malate may be further characterized by the XRPD pattern having characteristic peaks at 9.3, 13.3, 15.0, 19.5, 20.9, 22.8, 25.8, and 26.9(±)0.2° 2-theta.

Within the context of the present invention, the crystalline form-$M_4$ of cabozantinib (S)-malate may also be characterized by the PXRD pattern in FIG. 8.

The crystalline form-$M_4$ of cabozantinib (S)-malate may be additionally characterized by the DSC thermogram in FIG. 9.

According to the present invention, the crystalline form-$M_4$ of cabozantinib (S)-malate may be characterized by the TGA trace in FIG. 10.

Another aspect of the present invention provides the novel crystalline form-$M_1$ of cabozantinib free base.

One embodiment of the present invention provides a process for the preparation of crystalline form-$M_1$ of cabozantinib free base which includes the following steps:
 a) dissolving cabozantinib (S)-malate in a solvent to create a solution,
 b) adding water to the solution,
 c) adding ketone solvent, and
 d) isolating crystalline form-$M_1$ of cabozantinib free base.

According to the present invention, cabozantinib (S)-malate may be dissolved in a solvent to create a solution. Within the context of the present invention, the solvent may be, for example, N,N-dimethylacetamide, N,N-dimethylformamide, N-methyl-2-pyrrolidone, dimethyl sulfoxide, acetonitrile, dichloromethane, tetrahydrofuran, or ethyl acetate. In some embodiments of the present invention, N-methyl-2-pyrrolidone was found to be a particularly useful solvent.

Next, water may be added to the reaction mass followed by a ketone solvent. Within the context of the present invention, the ketone solvent may be, for example, acetone, methyl ethyl ketone, or methyl isobutyl ketone. In some embodiments of the present invention, acetone was found to be a particularly useful solvent. The crystalline form-$M_1$ of cabozantinib free base may then be isolated.

In particularly useful embodiments of the present invention, cabozantinib (S)-malate may be dissolved in a solvent, such as N-methyl-2-pyrrolidone, at a temperature between about 20° C. and about 35° C. Water may then be added to the clear solution. Next, a ketone solvent, for example, acetone, may be added, and the reaction mixture heated to about 45° C. to about 55° C. Water may then be added while the reaction mixture is maintained at a temperature between about 20° C. and about 35° C. The obtained solid may then be filtered to get the crystalline form-$M_1$ of cabozantinib free base.

Another embodiment of the present invention provides a process for the preparation of crystalline form-$M_1$ of cabozantinib free base, which includes the following steps:
 a) dissolving cabozantinib (S)-malate in a solvent to form a solution,
 b) adding water to the solution, and
 c) isolating the crystalline form-$M_1$ of cabozantinib.

According to the present invention, cabozantinib (S)-malate may be dissolved in a solvent to create a solution. The solvent may be, for example, N,N-dimethylacetamide, N,N-dimethylformamide, N-methyl-2-pyrrolidone, dimethyl sulfoxide, acetonitrile, dichloromethane, tetrahydrofuran, or ethyl acetate. In some embodiments of the present invention, dimethyl sulfoxide was found to be a particularly useful solvent. Next, water may be added to the reaction mass and the crystalline form-$M_1$ of cabozantinib may be isolated. In particularly useful embodiments of the present invention, cabozantinib (S)-malate may be dissolved in a solvent, for example, in dimethyl sulfoxide, at a temperature of about 20° C. to about 35° C. Water may then be added and the obtained solid is filtered to get the crystalline form-$M_1$ of cabozantinib free base.

According to the present invention, crystalline form-$M_1$ of cabozantinib free base may be characterized by the XRPD pattern having peaks at about 11.8(±)0.2° 2-theta.

Within the context of the present invention, crystalline form-$M_1$ of cabozantinib free base may be further characterized by the XRPD pattern having peaks at about 11.8, 12.8, 14.3, 17.8, and 22.7(±)0.2° 2-theta The crystalline form-$M_1$ of cabozantinib free base may be further characterized by the XRPD pattern as depicted in FIG. 11.

According to the present invention, the crystalline form-$M_1$ of cabozantinib free base may be characterized by the DSC thermogram in FIG. 12.

According to the present invention, the crystalline form-$M_1$ of cabozantinib free base may also be characterized by the TGA trace in FIG. 13.

Another aspect of the present invention provides the novel crystalline form-$M_2$ of cabozantinib free base.

One embodiment of the present invention provides a process for the preparation of crystalline form-$M_2$ of cabozantinib free base which includes the following steps:
 a) dissolving cabozantinib in a solvent,
 b) partially removing the solvent, and
 c) isolating the crystalline form-$M_2$ of cabozantinib free base.

According to the present invention, cabozantinib may be dissolved in a solvent. Within the context of the present invention, the solvent may be, for example, halogenated, alcoholic, or a mixture thereof. Suitable halogenated solvents include, for example, dichloromethane and dichloroethane. Suitable alcohols include, for example, methanol, ethanol, propanol, and butanol. In some embodiments of the present invention, a mixture of methanol and dichloromethane was found to be particularly useful. Next, some of the solvent is removed, for example by Evaporation, Heating and Distillation, preferably Distillation.

The crystalline form-$M_2$ of cabozantinib free base may then be isolated.

In particularly useful embodiments of the present invention, cabozantinib may be dissolved in a mixture of solvents, for example a mixture methanol and dichloromethane, at about 25° C. to about 45° C. The resulting clear solution may then be partially distilled out under atmospheric pressure to obtain a slurry. The slurry is then cooled to a temperature between about 20° C. and about 35° C. and filtered to get the crystalline form-$M_2$ of cabozantinib free base.

According to the present invention, crystalline form-$M_2$ of cabozantinib free base may be characterized by the XRPD pattern having peaks at about 12.6, 14.1, 18.5, 22.1, 23.2, 24.1, and 29.0(±)0.2° 2-theta.

Within the context of the present invention, the crystalline form-$M_2$ of cabozantinib free base may further characterized by the XRPD pattern having peaks at about 7.8, 11.1, 11.5, 12.6, 14.1, 15.4, 17.2, 18.5, 19.2, 21.1, 22.1, 23.2, 24.1, and 29.0(±)0.2° 2-theta The crystalline form-$M_2$ of cabozantinib free base may be further characterized by the XRPD pattern in FIG. 14.

The crystalline form-$M_2$ of cabozantinib free base may also be characterized by DSC thermogram in FIG. 15.

The crystalline form-$M_2$ of cabozantinib free base may also be characterized by the TGA trace as in FIG. 16.

Another aspect of the present invention provides the novel crystalline form-$M_3$ of cabozantinib free base.

One embodiment of the present invention provides a process for the preparation of crystalline form-$M_3$ of cabozantinib free base which includes the following steps:
 a) providing cabozantinib base in an ester solvent,
 b) removing the ester solvent,
 c) adding an ethereal solvent, and
 d) isolating the crystalline form-$M_3$ of cabozantinib free base.

According to the present invention, cabozantinib base may be provided in an ester solvent. Within the context of the present invention, the ester solvent may be, for example, methyl acetate, ethyl acetate, propyl acetate, or n-butyl acetate. In some embodiments of the present invention, ethyl acetate was found to be a particularly useful ester solvent. Next, the ester solvent may be substantially removed from the reaction mass, for example by Evaporation, Heating and Distillation, preferably Distillation.

Next, an ethereal solvent may be added. Suitable ethereal solvents include, as examples, dimethyl ether, diethyl ether, diisopropyl ether, ethyl methyl ether, methyl-tert-butyl ether, tetrahydrofuran, and 1,4-dioxane. In some embodiments of the present invention, diisopropyl ether was found to be a particularly useful ethereal solvent. Next, crystalline form-$M_3$ of cabozantinib free base may be isolated.

In particularly useful embodiments of the present invention, cabozantinib base may be provided in an ester solvent, for example, ethyl acetate, is provided. Next, the solvent may be distilled out. Next, an ethereal solvent, for example, diisopropyl ether, may be added to create a slurry. The obtained slurry may be filtered and dried under vacuum to get the crystalline form-$M_3$ of cabozantinib free base.

According to the present invention, crystalline form-$M_3$ of cabozantinib free base may be characterized by the XRPD pattern having peaks at about 15.5, 17.7, 19.6, and 21.1(±) 0.2° 2-theta.

Within the context of the present invention, the crystalline form-$M_3$ of cabozantinib free base may be further characterized by the XRPD pattern having peaks at about 4.9, 9.7, 12.0, 15.5, 17.7, 19.6, 21.1, 23.1, 24.1, and 26.6($\pm$)0.2° 2-theta The crystalline form-$M_3$ of cabozantinib free base may also be further characterized by the XRPD pattern in FIG. 17.

Another aspect of the present invention provides a process for the preparation of crystalline cabozantinib (S)-malate form N-1 which includes the following steps:
 a) providing cabozantinib base and (S)-malic acid in a first polar solvent,
 b) adding a second solvent to the reaction mass,
 c) seeding form N-1 of cabozantinib (S)-malate, and
 d) isolating the cabozantinib (S)-malate form N-1.

According to the present invention, cabozantinib base and (S)-malic acid may be provided in a first polar solvent. Within the context of the present invention, the first polar solvent may be, for example, methanol, ethanol, propanol, butanol, ethyl acetate, acetone, acetonitrile, dichloromethane, dimethylformamide, dimethyl sulfoxide, tetrahydrofuran, 1,4-dioxane, water, or mixtures thereof. In some embodiments of the present invention, a mixture of tetrahydrofuran and water was found to be particularly useful for this step.

Next, a second solvent may be added to the reaction mass. Within the context of the present invention, the second solvent may be a nitrile solvent, for example, acetonitrile. The solution may then be seeded with Form N-1 of cabozantinib (S)-malate, and Form N-1 of cabozantinib (S)-malate may then be isolated.

In some particularly useful embodiments of the present invention, cabozantinib base and (S)-malic acid may be added to a solvent, for example, a mixture of tetrahydrofuran and water. The suspension may then be heated to about 55° C. to about 65° C. and a second solvent, for example, acetonitrile, may be added to the reaction mass. A seed of form N-1 of cabozantinib (S)-malate may then be added to the solution which is then cooled to about 20° C. to about 35° C. The resulted solid may then be filtered and dried to get the crystalline form N-1 of cabozantinib (S)-malate.

With all of the reactions disclosed above, one of skill in the art will recognize that the reaction conditions (e.g., reaction time or temperature) may be adjusted to achieve appropriate yield without undertaking undue experimentation and without departing from the scope of the present disclosure.

In some embodiments, the cabozantinib polymorphs and cabozantinib free base polymorphs of the present invention may be included in capsules for oral administration. One of skill in the art will recognize a wide variety of pharmaceutically acceptable excipients that may be included in such a capsule formulation, including microcrystalline cellulose, croscarmellose sodium, sodium starch glycolate, fumed silica, and stearic acid. The capsule may have a shell which may contain one or more of the following ingredients: black iron oxide, red iron oxide, and titanium dioxide.

The cabozantinib polymorphs and cabozantinib free base polymorphs disclosed herein may be included in formulations prescribed for the treatment of medullary thyroid cancer and progressive, metastatic medullary thyroid cancer, in particular. The cabozantinib polymorphs and cabozantinib free base polymorphs disclosed herein may be formulated as a solid dosage form, such as a capsule, containing about 20 mg to about 80 mg per capsule for administration to patients.

In view of the above description and the examples below, one of ordinary skill in the art will be able to practice the invention as claimed without undue experimentation. The foregoing will be better understood with reference to the following examples that detail certain procedures for the preparation of molecules, compositions and formulations according to the present invention. All references made to these examples are for the purposes of illustration. The following examples should not be considered exhaustive, but merely illustrative of only a few of the many aspects and embodiments contemplated by the present disclosure.

EXAMPLES

Example 1: Preparation of Cabozantinib (S)-Malate Crystalline Form-$M_1$

Cabozantinib base (2 g) and (S)-malic acid (0.64 g) were dissolved in a mixture of THF (24 ml) and water (2 ml) at 60-65° C. and the reaction mass was cooled to room temperature. The resulting clear solution was added to n-heptane (80 ml) at 25-30° C. and stirred at room temperature for 2 hours. The solid obtained was filtered and dried under vacuum at 45° C. for 5 hours. The product obtained was identified as cabozantinib (S)-malate crystalline form-$M_1$.

Example 2: Preparation of Cabozantinib (S)-Malate Crystalline Form-$M_1$

Cabozantinib (S)-malate (1.0 g) was dissolved in THF (6 ml) and water (0.2 ml) mixture at 60-65° C. and then cooled to room temperature. The resulting clear solution was added to n-heptane (30 ml) solution at 25-30° C. and maintained under agitation at room temperature for 2 hours. The solid obtained was filtered and dried under vacuum at 45° C. for 5 hours. The product obtained was identified as cabozantinib (S)-malate crystalline form-$M_1$.

Example 3: Preparation of Cabozantinib (S)-Malate Crystalline Form-$M_1$

Cabozantinib (S)-malate (3 g) was dissolved in THF (36 ml) and water (3 ml) mixture at 60-65° C. and then cooled to room temperature. The resulting clear solution was added to n-heptane (120 ml) solution at 25-30° C. and stirred at room temperature for 1-2 hours. The solid obtained was filtered and dried under vacuum at 45° C. for 5 hours. The product obtained was identified as cabozantinib (S)-malate crystalline form-$M_1$.

Example 4: Preparation of Cabozantinib (S)-Malate Crystalline Form-$M_2$

Cabozantinib (S)-malate (0.5 g) was dissolved in propionic acid (1.5 ml) at 50° C. and then cooled to 25-30° C. The resulting clear solution was kept at room temperature for overnight without agitation, methyl-t-butyl ether (15 ml) was added, and the solution was stirred for 60 min. The obtained solid was filtered and dried under vacuum at 70° C. for 10 hours. The product obtained was identified as cabozantinib (S)-malate crystalline form-$M_2$.

Example 5: Preparation of Cabozantinib (S)-Malate Crystalline Form-$M_3$

Cabozantinib (S)-malate (100 mg) was dissolved in acetic acid (0.2 ml) at 60° C. The resulting clear solution was kept at room temperature for 15 hours, cooled to 0-5° C., then water (5 ml) was added and stirred for 10 min. The solid obtained was filtered and washed with water (1 ml). The product obtained was identified as cabozantinib (S)-malate crystalline form-$M_3$.

Example 6: Preparation of Cabozantinib (S)-Malate Crystalline Form-$M_4$

Cabozantinib free base (1 g) and (S)-malic acid (0.32 g) were dissolved in a mixture of THF (15 ml) and water (1 ml) at 60-65° C. for 60 minutes and the reaction mass was cooled to room temperature. The resulting clear solution was added to an n-heptane solution (15 ml) at 50-55° C. and maintained under agitation for 120 minutes. The resulting reaction mass was cooled to 25-30° C. and maintained for 60 minutes The obtained solid was filtered and washed with n-heptane (10 ml). The resulted product was dried under vacuum at 60° C. for 180 minutes. The obtained product was identified as cabozantinib (S)-malate crystalline form-$M_4$.

Example 7: Preparation of Cabozantinib (S)-Malate Crystalline Form-$M_4$

Cabozantinib (S)-malate (50 mg) was dissolved in N,N-dimethylacetamide (0.5 ml) at 50° C. and the resulting clear solution was kept at room temperature for 2 days without agitation. Methyl-t-butyl ether (8 ml) and ethanol (0.5 ml) were then added and the solution was kept at room temperature for 2 days. To the resulting layer, ethanol (5 ml) was added and kept at room temperature for 7 days without agitation. The solid obtained after solvent evaporation was identified as cabozantinib (S)-malate crystalline form-$M_4$.

Example 8: Preparation of Cabozantinib Free Base Crystalline Form-$M_1$

Cabozantinib (S)-malate (50 mg) was dissolved in 1-methyl-2-pyrrolidone (0.5 ml) at 25-30° C. and maintained at 25-30° C. for 2 days without agitation. Water (5 ml) was added to the clear solution resulting in a suspension. Acetone (3 ml) was added to the suspension and heated to 50° C. to get clear solution. Water (5 ml) was added to the clear solution under agitation and maintained at 25-30° C. for 2 hours without agitation. The solid obtained was filtered and identified as cabozantinib free base crystalline form-$M_1$.

Example 9: Preparation of Cabozantinib Free Base Crystalline Form-$M_1$

Cabozantinib (S)-malate (50 mg) was dissolved in DMSO (0.5 ml) at 25-30° C. and maintained at 25-30° C. for 2 days without agitation. Water (5 ml) was then added under agitation and maintained at 25-30° C. for 24 hours. The obtained solid was filtered and identified as cabozantinib free base crystalline form-$M_1$.

Example 10: Preparation of Cabozantinib Free Base Crystalline Form-$M_2$

Cabozantinib base (12.0 g) was dissolved in a methanol (120 ml) and dichloromethane (120 ml)) mixture at 28-38° C. Charcoal (10%) was added to the resulting clear solution, and the reaction mass was filtered through celite bed. The obtained clear filtrate was distilled under atmospheric pressure at 40-45° C. The distillation continued until about 10 volumes (120 ml) of solution along with the solid remained inside. The slurry was cooled to 25-30° C. Then after the slurry was stirred at 25-30° C. room temperature for 1.0 hours. The product was filtered and dried under vacuum at 50-55° C. for 2 hours. The product obtained was identified as non-solvated crystalline cabozantinib free base form-$M_2$.

Example 11: Preparation of Cabozantinib Free Base Crystalline Form-$M_3$

1-[4-(6,7-dimethoxy-quinolin-4-yloxy)-phenylcarbamoyl]-cyclopropanecarboxylic acid (2.0 g) was reacted with 4-fluoroaniline hydrochloride (1.08 g) in presence of EDC-HCl (2.8 g), 1-hydroxybenztriazole (1.98 g), and diisopropylethylamine (5 ml) in N,N-dimethylformamide (20 ml). The reaction was stirred overnight. After overnight stirring, the reaction mass was quenched with water (60 ml). The cabozantinib base was extracted with ethyl acetate (80 ml). Ethyl acetate was distilled out completely and diisopropyl ether (30 ml) was added. The slurry obtained was filtered and dried under vacuum at 60° C. for 2 hours. The product obtained was identified as cabozantinib free base form-$M_3$.

Example 12: Process for Preparation of Cabozantinib Form N-1

1.5 g of cabozantinib base and 0.48 g of (S)-malic acid were added in a mixture of THF (18.0 ml) and water (1.5 ml) at 25-30° C. The reaction mass was heated at 60° C. The clear solution was maintained at 60° C. for 1 hour. The reaction mass was filtered through filter paper followed by 0.45 micron paper. The clear filtrate was heated again to 60° C. at which point acetonitrile was added over a period of 60 minutes. After acetonitrile was added, a 50 mg seed of form N-1 of cabozantinib (S)-malate was added. The reaction suspension was maintained at 60° C. for 4 h. After 4 hours of heating, the reaction mass was cooled to 25-30° C. and stirred for 30 minutes. The product was filtered and washed with 18 ml of acetonitrile. The product was vacuum dried for 30 minutes followed by drying under vacuum at 60-60° C. for 3 hours. The cabozantinib (S)-malate was identified as form N-1.

Example 13: Process for Preparation of Amorphous Cabozantinib-(S)-Malate 100 mg of cabozantinib (S)-malate obtained by the process in example 3 was kept in a static dryer and heated at 110-120° C. under vacuum for 20-30 min. The resulting solid was identified as amorphous cabozantinib (S)-malate.

We claim:

1. Crystalline polymorph form-$M_4$ of cabozantinib (S)-malate, which is characterized by an X-ray powder diffraction pattern substantially as shown in FIG. 8 or a thermogravimetric analysis pattern substantially as shown in FIG. 9.

2. Crystalline polymorph form-$M_4$ of cabozantinib (S)-malate, which has an X-ray powder diffraction pattern with significant peaks at about 2θ values of 9.3, 13.3, 15.0, 22.8, and 25.8(±)0.2°.

3. A process for the preparation of crystalline form-$M_4$ of cabozantinib (S)-malate of claim 2 comprising the steps of:
   a) dissolving cabozantinib base and (S)-malic acid in a solvent to create a solution;
   b) adding the solution to a non-polar solvent; and
   c) isolating crystalline form-$M_4$ of cabozantinib (S)-malate.

4. The process according to claim 3, wherein the solvent is selected from an ethereal solvent, an alcoholic solvent, water, or mixtures thereof.

5. The process according to claim 4, wherein the ethereal solvent is selected from the group consisting of dimethyl ether, diethyl ether, ethyl methyl ether, methyl-tert-butyl ether, tetrahydrofuran, and 1,4-dioxane.

6. The process according to claim 4 wherein the alcoholic solvent is selected from the group consisting of methanol, ethanol, propanol, and butanol.

7. The process according to claim 4, wherein the solvent is a mixture of tetrahydrofuran and water.

8. The process according to claim 7, wherein the mixture of tetrahydrofuran and water are exist in a ratio of 15:1.

9. The process according to claim 3, wherein the non-polar solvent is selected from the group consisting of C1-C10 alkanes or a mixture of C1-C10 alkanes.

10. The process according to claim 9, wherein non-polar solvent is n-heptane.

11. A process for the preparation of crystalline form-$M_4$ of cabozantinib (S)-malate of claim 2 comprising the steps of:
   a) dissolving cabozantinib (S)-malate in an amide solvent to create a reaction mixture;
   b) adding a solvent to the reaction mixture; and
   c) isolating the crystalline form-$M_4$ of cabozantinib (S)-malate.

12. The process according to claim 11, wherein the amide solvent is selected from the group consisting of N, N-dimethylacetamide, N, N-dimethylformamide, and N-methylpyrrolidone.

13. The process according to claim 12 where the amid solvent is N, N-dimethylacetamide.

14. The process according to claim 11, wherein the solvent selected from the group consisting of an ethereal solvent, an alcoholic solvent, and mixtures thereof.

15. The process according to claim 14, wherein the ethereal solvent is selected from the group consisting of dimethyl ether, diethyl ether, ethyl methyl ether, methyl-t-butyl ether, tetrahydrofuran, and 1,4-dioxane.

16. The process according to claim 14 wherein the alcoholic solvent is selected from the group consisting of methanol, ethanol, propanol, and butanol.

17. The process according to claim 14, wherein the solvent is a mixture of methyl-t-butyl ether and ethanol.

* * * * *